(12) United States Patent
Rami et al.

(10) Patent No.: US 6,939,891 B2
(45) Date of Patent: Sep. 6, 2005

(54) HETEROCYCLIC UREAS, THEIR PREPARATION AND THEIR USE AS VANILLOID RECEPTOR ANTAGONISTS

(75) Inventors: Harshad Kantilal Rami, Harlow (GB); Mervyn Thompson, Harlow (GB); Paul Adrian Wyman, Harlow (GB)

(73) Assignee: SmithKline Beecham, PLC, Brentford Middlesex (GB)

( * ) Notice: Subject to any disclaimer, the term of this patent is extended or adjusted under 35 U.S.C. 154(b) by 0 days.

(21) Appl. No.: 10/475,937

(22) PCT Filed: May 2, 2002

(86) PCT No.: PCT/EP02/04802

§ 371 (c)(1),
(2), (4) Date: Mar. 31, 2004

(87) PCT Pub. No.: WO02/090326

PCT Pub. Date: Nov. 14, 2002

(65) Prior Publication Data

US 2004/0171639 A1 Sep. 2, 2004

(30) Foreign Application Priority Data

May 2, 2001 (GB) .............................................. 0110901

(51) Int. Cl.$^7$ ...................... A61K 31/40; C07D 207/09; C07D 207/14

(52) U.S. Cl. ...................... 514/426; 514/428; 548/557; 548/567

(58) Field of Search ................................ 546/224, 231; 548/557, 568, 567; 514/329, 331, 426, 428

(56) References Cited

U.S. PATENT DOCUMENTS 3,424,760 A   1/1969   Helsley et al.
3,424,761 A   1/1969   Helsley et al.

OTHER PUBLICATIONS

Pan P–C et al., "Soluble Polymer–Supported Synthesis of Arylpiperazines" Tetrahedron Letters, Elsevier Science Publishers, Amsterdam, NL, vol. 39, No. 51, Dec. 17, 1998, pp. 9505–9508, XP004144238.

Hesley et al., "Synthesis and biological activity of some 1–substituted 3–pyrrolidinylureas" Journal of Medicinal Chemistry, vol. 11, No. 5, 1968, pp. 1034–1037, XP001095126.

*Primary Examiner*—Fiona T. Powers
(74) *Attorney, Agent, or Firm*—Soma G. Simon; Mary McCarthy; Charles Kinzig

(57) ABSTRACT

The invention relates to certain novel compounds having Vanilloid Receptor (VR1) antagonist activity, processes for their preparation, to compositions containing them and to their use in the treatment of various disorders.

3 Claims, No Drawings

HETEROCYCLIC UREAS, THEIR PREPARATION AND THEIR USE AS VANILLOID RECEPTOR ANTAGONISTS

This invention relates to novel compounds and in particular to urea derivatives having pharmacological activity, processes for their preparation, to compositions containing them and to their use in medicine.

Vanilloids are a class of natural and synthetic compounds which are characterised by the presence of a vanillyl (4-hydroxy 3-methoxybenzyl) group or a functionally equivalent group. Vanilloid Receptor (VR1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in EP 347000, EP 401903, GB 2226313 and WO 92/09285. Particularly notable examples of vanilloid compounds or vanilloid receptor modulators are capsaicin, namely trans 8-methyl-N-vanillyl-6-nonenamide, isolated from the pepper plant, capsazepine (Tetrahedron, Vol. 53, No. 13, pp. 4791–4814, 1997) and olvanil-N-(4-hydroxy-3-methoxybenzyl)oleamide (J. Med. Chem. 1993, 36, 2595–2604).

U.S. Pat. Nos. 3,424,760 and 3,424,761 both describe a series of 3-Ureidopyrrolidines that are said to exhibit analgetic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Applications, publication numbers WO02/08221, WO02/16317, WO02/16318 and WO02/16319 each disclose certain vanilloid receptor antagonists and their use for the treatment of diseases associated with the activity of vanilloid receptor.

A structurally novel class of compounds has now been found which possess vanilloid receptor (VR1) antagonist activity. They are therefore potentially useful in the treatment and/or prophylaxis of diseases or disorders mediated by or associated with the activity of the vanilloid receptor.

The present invention therefore provides, in a first aspect, a compound of formula (I) or a salt thereof or a solvate thereof:

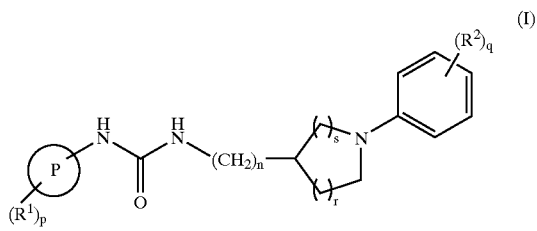

wherein:
P is phenyl or naphthyl;
$R^1$ and $R^2$ are independently selected from —H, —halo, —CN, —NO$_2$, —OH, —CF$_3$, —OCF$_3$, —NR$^4$R$^5$, —S(O)$_m$R$^6$, —S(O)$_2$NR$^4$R$^5$, —OS(O)$_2$R$^6$, —OS(O)$_2$CF$_3$, alkyl, cycloalkyl, alkoxy, —O(CH$_2$)$_n$NR$^4$R$^5$, —C(O)CF$_3$, —C(O)alkyl, —C(O)cycloalkyl, —C(O)alkylaryl, —C(O)aryl, —C(O)(CH$_2$)$_n$OR$^6$, —C(O)(CH$_2$)$_n$NR$^4$R$^5$, —C(O)Oalkyl, —C(O)NR$^4$R$^5$, —(CH$_2$)$_n$C(O)Oalkyl, —(CH$_2$)$_n$OC(O)R$^6$, —(CH$_2$)$_n$OR$^6$, —(CH$_2$)$_n$NR$^4$R$^5$, —(CH$_2$)$_n$C(O)NR$^4$R$^5$, —(CH$_2$)$_n$N(R$^4$)C(O)R$^6$, —(CH$_2$)$_n$S(O)$_2$NR$^4$R$^5$, —(CH$_2$)$_n$(R$^4$)S(O)$_2$R$^6$, —ZAr, arylalkyl-, arylalkoxy-, cycloalkylalkyl-, cycloalkylalkoxy-, R$^6$S(O)$_2$C$_{1-6}$alkyl-, R$^6$S(O)$_2$C$_{1-6}$alkoxy-, R$^6$S(O)$_2$N(R$^4$)—, R$^6$C(O)N(R$^4$)—, R$^6$S(O)$_2$N(R$^4$)C$_{1-6}$alkyl-, R$^6$C(O)N(R$^4$)C$_{1-6}$alkyl- or R$_6$C(O)C$_{1-6}$alkyl;

$R^4$ and $R^5$ may be the same or different and represent H or alkyl or $R^4$ and $R^5$ together with the atoms to which they are attached form an optionally substituted, saturated ring having 3 to 6 atoms optionally comprising a further nitrogen atom and/or a moiety NR$^6$;
$R^6$ is $C_{1-6}$-alkyl or aryl;
n is 0, 1, 2 or 3;
p is 0, 1, 2 or 3 and when p is 2 or 3 the groups $R^1$ can be the same or different;
q is 0, 1, 2 or 3 and when q is 2 or 3 the groups $R^2$ can be the same or different;
r is 1, 2 or 3; and
s is 0, 1 or 2;
and provided that the compound of formula (I) is not 1-(1-phenyl-3-pyrrolidinyl)-3-phenyl urea or 1-(1-phenyl-3-pyrrolidinyl)-3-(4-methoxyphenyl)urea Suitably a compound of formula (I) excluding 1-(1-phenyl-3-pyrrolidinyl)-3-phenyl urea and 1-(1-phenyl-3-pyrrolidinyl)-3-(4-methoxyphenyl)urea is a compound of formula (I').

Suitable, optionally substituted, saturated 3–6 membered rings include $C_{3-6}$azacycloalkane, or $C_{5-8}$ polymethylene rings.

Suitable optional substituents for saturated 3–6 membered rings includes one or more, suitably one, oxo groups One particular $C_{3-6}$azacycloalkane ring is a $C_{3-6}$(2-oxo) azacycloalkane ring.

Preferably P is phenyl.

When p is 1, 2 or 3, $R^1$ is preferably halogen, alkyl (particularly methyl), alkoxy (particularly methoxy), alkylthio (particularly thiomethyl), C(O)alkyl particularly acetyl), nitro, CF$_3$, CN or OCF$_3$.

Preferably P is 1 or 2.

Preferably n is 0 or 1, most preferably 0.

When q is 1, 2 or 3, $R^2$ is preferably halogen particularly fluoro or chloro) or alkyl (particularly methyl). Preferably q is 1 or 2. When q is 1, particularly preferred examples are 3-methyl and 3-fluoro. When q is 2, particularly preferred examples are 3,4-difluoro, 3-fluoro-4-methyl and 3-methyl-4-fluoro.

Suitably r and s have values such that they provide a 4–7 membered ring.

Preferably r and s have values such that they provide a 5 or 6 membered ring, most preferably a 5 membered ring.

Particular compounds according to this invention include examples E1–27 (as shown below) or a salt thereof or a solvate thereof.

Suitable salts include pharmaceutically acceptable salts.

Suitable solvates include pharmaceutically acceptable solvates. Suitable pharmaceutically acceptable salts include acid addition salts.

As indicated the compounds of formula (I) can form acid addition salts. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid.

As indicated the compounds of formula (I) may be prepared in crystalline or non-crystalline form, and, if crystalline, may optionally be solvated.

Suitable solvates include hydrates.

Suitable solvates include pharmaceutically acceptable solvates, such as pharmaceutically acceptable hydrates.

This invention includes within its scope stoichiometric solvates, such as hydrates, as well as non-stoichiometric solvates, such as hydrates.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

When used herein "alkyl" whether used alone or as part of another group refers to straight chain or branched chain alkyl groups, such as $C_{1-12}$alkyl or $C_{1-6}$alkyl. A preferred akyl group is $C_{1-6}$alkyl.

When used herein "cycloalkyl" whether used alone or as part of another group refers to single or fused cycloalkyl groups wherein each ring comprises up to 12 carbon atoms, suitably 3 to 6 carbon atoms. A preferred cycloalkyl group is a $C_{3-6}$alkyl group.

The term 'halogen' is used herein to describe, unless otherwise stated, a group selected from fluorine, chlorine, bromine or iodine.

The term 'aryl' is used herein to describe, unless otherwise stated, phenyl or naphthyl.

Optional substituents for any aryl group include up to three groups selected from: alkyl, hydroxy, alkyloxy, CN, $OCF_3$, alkylhalogen, alkylthio, alkylsulfinyl, alkylsulfonyl, nitro, amino, mono- or dialkylamino and C(O)alkyl groups.

A suitable alkylhalogen group is a $CF_3$ group.

The term 'naphthyl' is used herein to denote, unless otherwise stated, both naphthalen-1-yl and naphthalen-2-yl groups.

The present invention also provides a process for the preparation of a compound of formula (I') or a salt thereof or a solvate thereof, which process comprises coupling a compound of formula (II):

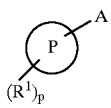

(II)

in which $R^1$, P and p are as defined in formula (I) with a compound of formula (III):

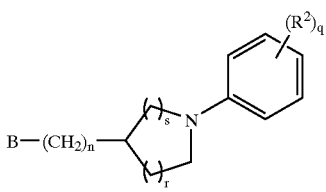

(III)

in which $R^2$, n, q, r and s are as defined in formula (I) and A and B contain appropriate functional groups which are capable of reacting together to form the urea moiety; and thereafter, carrying out one or more of the following optional steps:
(i) removing any protecting groups
(ii) converting $R^1$ into another $R^1$ or $R^2$ into another $R^2$; and
(iii) forming a salt of a compound of formula (I') or a solvate of a compound of formula (I).

Suitable examples of appropriate A and B groups include:
(a) A is —N=C=O and B is $NH_2$; or A is $NH_2$ and B is N=C=O or
(b) A is $NH_2$ and B is $NH_2$ together with an appropriate urea forming agent.

In process (a) or (c), that is when A is —N=C=O and B is $NH_2$ or vice versa, the reaction is carried out in an inert solvent such as dichloromethane or acetonitrile.

In process (b) the reaction is preferably carried out in the presence of an appropriate urea forming agent, such as carbonyl diimidazole or phosgene, a suitable solvent being an inert organic solvent such as dimethylformamide, tetrahydrofuran, or dichloromethane at ambient or elevated temperature optionally in the presence of a base such as triethylamine or pyridine.

An alternative method of synthesis of the unsymmetrical urea compounds of formula (I') is from a diaryl carbonate, via the corresponding carbamate. Such a methodology is described by Freer et al. (Synthetic Communications, 26(2), 331–349, 1996). It would be appreciated by those skilled in the art that such a methodology could be readily adapted for preparation of the compounds of formula (I).

The above mentioned optional proces steps (1), (2) or (3) are carried out using the appropriate conventional methods, for example those disclosed in standard reference texts such as Comprehensive Organic Transformations, R. C. Larock, Wiley-VCH (Chichester), 1999.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl, tert-butyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

Compounds of formulae (II) and (III) are commercially available, or they may be prepared by procedures described herein, by known methods or by analogous procedures thereto.

Salts including pharmaceutically acceptable salts may be prepared by use of appropriate conventional methods, such as treating a compound of formula (I) with an appropriate salting agent, for example the preparation of acid addition salts is conveniently effected by treatment with an appropriate acid or acid derivative.

Solvates including pharmaceutically acceptable solvates may be prepared by use of appropriate conventional methods.

As indicated above, the compounds of formula (I) and their pharmaceutically acceptable salts or pharmaceutically acceptable solvates have Vanilloid receptor antagonist (VR1) activity and are believed to be of potential use for the treatment or prophylaxis of certain diseases or disorders mediated or associated with the activity of vanilloid receptor, including disorders such as pain, chronic pain, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, emesis, stomach duodenal ulcer and pruritus.

Thus the invention also provides a compound of formula (I') or a pharmaceutically acceptable salt thereof, for use as an active therapeutic substance, in particular in the treatment or prophylaxis of diseases or disorders mediated or associated with the activity of vanilloid receptor. In particular the invention provides a compound of formula (I') or a pharmaceutically acceptable salt thereof for use in the treatment or prophylaxis of pain.

The invention further provides a method of treatment or prophylaxis of diseases or disorders mediated or associated with the activity of vanilloid receptor, in mammals including humans, which comprises administering to the sufferer a therapeutically effective amount of a compound of formula (I').

The invention provides for the use of a compound of formula (I') or a pharmaceutically acceptable salt thereof or a pharmaceutically acceptable solvate thereof in the manufacture of a medicament for the treatment or prophylaxis of diseases or disorders mediated or associated with the activity of vanilloid receptor.

In order to use the compounds of formula (I) in therapy, they will normally be formulated into a pharmaceutical composition in accordance with standard pharmaceutical practice. Accordingly, the present invention also provides a pharmaceutical composition, which comprises a compound of formula (I') or a pharmaceutically acceptable salt thereof or a pharmaceutically acceptable solvate thereof and a pharmaceutically acceptable carrier or excipient.

A pharmaceutical composition of the invention, which may be prepared by admixture, suitably at ambient temperature and atmospheric pressure, is usually adapted for oral, parenteral, rectal administration or intravesical adminstration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof or a pharmaceutically acceptable solvate thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filing into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three times a day, so that the total daily dosage is in the range of about 0.5 to 1000 mg; and such therapy may extend for a number of weeks or months.

All publications, including but not limited to patents and patent applications, cited in this specification are herein incorporated by reference as if each individual publication were specifically and individually indicated to be incorporated by reference herein as though filly set forth.

The following Descriptions and Examples illustrate the invention but do not limit it in any way.

Description 1

(R)-2-Hydroxymethylpyrrolidine-1-carboxylic acid benzyl ester (D1)

To a solution of R-(−)-pyrrolidinemethanol (5 g, 0.05 mol) and triethylamine (2 eq., 14 ml) in DCM(30 ml) was added dropwise a solution of benzyl chloroformate in DCM (20 ml) at ambient temperature. After stirring for 4 h the DCM solution was partitioned with water (50 ml) and the organic phase separated, dried over anhydrous $MgSO_4$, and concentrated under reduced pressure. The crude product was chromatographed on silica gel eluting with EtOAc to afford a clear oil (9.76 g, 81%).

Description 2

(R)-2-(tert-Butyldimethylsilyloxymethyl) pyrrolidine-1-carboxylic acid benzyl ester (D2)

A solution of D1 (9.70 g, 0.04 mol), imidazole (1.05 eq., 2.95 g) and tert-butyldimethylsilyl chloride (1.1 eq., 6.22 g) in DMF (dry, 50 ml) was stirred overnight at ambient temperature. Solvent was removed under reduced pressure and the residue partitioned between $Et_2O$ and water. The aqueous phase was separated and the organic phase washed with dilute HCl (0.5M, 2×100 ml), followed by water (2×100 ml) and the organic phase was then dried (anhydrous $MgSO_4$), filtered and concentrated under reduced pressure to afford an oil (12.70 g). This was used in the next step without purification.

Description 3

(R)-2-(tert-Butyldimethylsilyloxymethyl)pyrrolidine (D3)

To a solution of D2 (12.7 g, 0.036 mol) and cyclohexene (excess, 20 ml) in ethanol (100 ml) was added 10% palladium on charcoal catalyst. Reaction was heated at reflux overnight and cooled. Catalyst was filtered and the filtrate concentrated to leave an oil (6.69 g) which was used in the next step without purification.

Description 4

(R)-2-(tert-Butyldimethylsilyloxymethyl)1-(3-methylphenyl)pyrrolidine (D4)

A suspension of cesium carbonate (1.5 eq., 15.2 g), palladium acetate (10 mol %, 0.69 g) and BINAP (15 mol %, 2.90 g) in 1,4-dioxane (dry, 50 ml) was sonicated for 45 min. To the resulting dark pink suspension was added a solution of D3 (6.60 g, 0.03 mol) and 3-bromotoluene (2 eq., 10.60 g) in 1,4dioxane (dry, 30 ml). The reaction was heated at 100 C for 18 h and cooled. Solvent was removed under reduced pressure and the residue partitioned between DCM and water. Organic phase was separated, dried over $MgSO_4$, filtered and concentrated under reduced pressure to leave an oil. Chromatography on silica gel eluting with EtOAc in hexane (gradient elution, maximum 5%) afforded the product as an oil (7.24 g, 77%).

Description 5

((R)-1-(3-Methylphenyl)pyrrolidin-2-yl)methanol (D5)

A solution of D4 (7.20 g, 0.024 mol) in THF (50 ml) was treated with tetrabutylammonium fluoride (1M solution in THF, 2 eq., 96 ml) and then stirred at ambient temperature for 18 h. Solvent was removed under reduced pressure and residue chromatographed on silica gel eluting with EtOAc in hexane (gradient elution, maximum 50%) to afford the product as an oil (3.70 g, 81%).

Description 6

2-((R)-1-(3-Methylphenyl)pyrrolidin-2-ylmethyl) isoindole-1,3-dione (D6)

To a suspension of phthalimide (1.1 eq., 3.14 g), triphenylphosphine (1.1 eq., 5.59 g) and D5 (3.70 g, 0.019 mol) in THF (50 ml) was added dropwise diisopropyl azodicarboxylate (1.1 eq., 4.20 ml). Reaction was stirred for 18 h at ambient temperature and then solvent removed under pressure. The crude product was chromatographed on silica gel eluting with EtOAc in hexane (gradient elution, maximum 10%) to afford the product as an oil (5.89, 95%).

Description 7

((R)-1-(3-Methylphenyl)pyrrolidin-2-yl) methylamine (D7)

A solution of D6 (5.80 g, 0.018 mol) in ethanol (60 ml) and hydrazine hydrate (2 .eq., 2 ml) was heated at reflux for 1 h and cooled. The resulting precipitate was filtered and filtrate concentrated under reduced pressure to leave an oil. Chromatography on silica gel eluting with methanol in DCM (gradient elution, maximum 10%) afforded the product as an oil (3.58 g, 94%).

Description 8

(S)-2-Hydroxymethylpyrrolidine-1-carboxylic acid benzyl ester (D8)

The title compound was prepared from (S)-(+)-2-pyrrolidinemethanol using the procedure outlined for Description 1 (10.21 g, 92%).

Description 9

(S)-2-(tert-Butyldimethylsilyloxymethyl)pyrrolidine-1-carboxylic acid benzyl ester (D9)

The title compound was prepared from D8 using the procedure outlined for Description 2 (14.93, 99%).

Description 10

(S)-2-(tert-Butydimethylsilyloxymethyl)pyrrolidine (D10)

The title compound was prepared from D9 using the procedure outlined for Description 3 (7.69 g, 83%).

Description 11

(S2(tert-Butyldimethylsilyloxymethyl)-1-(3-methylphenyl)pyrrolidine (D11)

The title compound was prepared from D10 using the procedure outlined for Description 4 (2.74 g, 50%).

Description 12

((S)-1-(3-Methylphenyl)pyrrolidin-2-yl)methanol (D12)

The title compound was prepared from D11 using the procedure outlined for Description 5 (1.57 g, 95%).

Description 13

2-((S)-1-(3-Methylphenyl)pyrrolidin-2-ylmethyl) isoindole-1,3-dione (D13)

The title compound was prepared from D12 using the procedure outlined for Description 6 (2.27 g, 87%).

Description 14

((S)-1-(3-Methylphenyl)pyrrolidin-2-yl)methylamine (D14)

The desired product was prepared from D13 using the procedure outlined for Description 7 (1.06 g, 82%).

Description 15

(S)-1-((3-Methylphenyl)pyrrolidin-3-yl)carbamic acid tert-butyl ester (D15)

The title compound was prepared from (3S)-(−)-3-(tert-butyloxycarbonylamino) pyrrolidine (TCI, Japan) and 3-bromotoluene using the procedure outlined for Description 4 (2.15 g, 60%).

Description 16

(S)-1-(3-Methylphenyl)pyrrolidin-3-ylamine (D16)

A solution of D15 (2.10 g, 7.6 mmol) in DCM (20 ml) and trifluoroacetic acid (5 eq., 2.9 ml) was heated at 40° C. for 18 h and cooled. The reaction was then partitioned with aqueous sodium hydrogen carbonate (10%, 50 ml) and the organic phase separated. Addition of anhydrous $MgSO_4$ followed by filtration and concentration of filtrate under reduced pressure afforded the crude product. Bulb to bulb distillation under reduced pressure afforded the product as a clear oil (0.89 g, 68%).

Description 17

(R)-1-((3-Methylphenyl)pyrrolidin-3-yl)carbamic acid tert-butyl ester (D17)

The title compound was prepared from 3R-(+)-3-(tert-butyloxycarbonylamino) pyrrolidine (TCI Japan) and 3-bromotoluene using the procedure outlined in Description 4 (2.08 g, 58%).

Description 18

(R)-1-(3-Methylphenyl)pyrrolidin-3-ylamine (D18)

The title compound was prepared from D17 using the procedure outlined for Description 16 and the isolated product was used without purification (1.03 g, 78%).

Description 19

(R)-1-((3-Fluorophenyl)pyrrolidin-3-yl)carbamic acid tert-butyl ester (D19)

The title compound was prepared from 3R-(+)-3-(tert-butyloxycarbonylamino) pyrrolidine (TCI, Japan) and 1-bromo-3-fluorotoluene using the procedure outlined in Description 4 (3.20 g, 88%).

Description 20

(R)-1-(3-Fluorophenyl)pyrrolidin-3-ylamine (D20)

The title compound was prepared from D19 using the procedure outlined for Description 16 (1.68 g, 85%).

Description 21

(R)-1-((3-Fluoro-4-methylphenyl)pyrrolidin-3-yl) carbamic acid tert-butyl ester (D21)

The title compound was prepared from 3R-(+)-3-(tert-butyloxycarbonylamino) pyrrolidine (TCI Japan) and 2-fluoro-4-bromotoluene using the procedure outlined in Description 4 (25.40 g, 62%).

Description 22

(R)-1-(3-Fluoro-4-methylphenyl)pyrrolidin-3-ylamine (D22)

The title compound was prepared from D21 using the procedure outlined for Description 16 (5.40 g, 85%).

Description 23

(R)-1-((3,4-Difluorophenyl)pyrrolidin-3-yl)carbamic acid tert-butyl ester (D23)

The title compound was prepared from 3R-+)-3-(tert-butyloxycarbonylamino) pyrrolidine (TCI, Japan) and 4-bromo-1,2-fluorobenzene using the procedure outlined in Description 4 (11.20 g, 78%).

Description 24

(R)-1-(3,4-Difluorophenyl)pyrrolidin-3-ylamine (D24)

The title compound was prepared from D23 using the procedure outlined for Description 16 (6.40 g, 77%).

Description 25

(R)1-((4-Fluoro-3-methylphenyl)pyrrolidin-3-yl) carbamic acid tert-butyl ester (D25)

The title compound was prepared from 3R-(+)-3-tert-butyloxycarbonylamino) pyrrolidine (TCI Japan) and 5-bromo-2-fluorotoluene using the procedure outlined in Description 4 (0.25 g, 31%).

Description 26

(R)-1-((4-Fluoro-3-methylphenyl)pyrrolidin-3-ylamine (D26)

The title compound was prepared from D25 using the procedure outlined for Description 16 (0.14 g, 91%).

Description 27

(S)-1-((3-Fluorophenyl)pyrrolidin-3-yl)carbamic acid tert-butyl ester (D27)

The title compound was prepared from 3S-(−)-3-(tert-butyloxycarbonylamino) pyrrolidine (TCI, Japan) and 1-bromo-3-fluorotoluene using the procedure outlined in Description 4 (0.17 g, 55%).

Description 28

(S)-1-(3-Fluorophenyl)pyrrolidin-3-ylamine (D28)

The title compound was prepared from D26 using the procedure outlined for Description 16 (0.078 g, 71%).

EXAMPLE 1

N-(4-Fluorophenyl)-N'-[(R)-1-((3-methylphenyl) pyrrolidin-2-ylmethyl)]urea (E1)

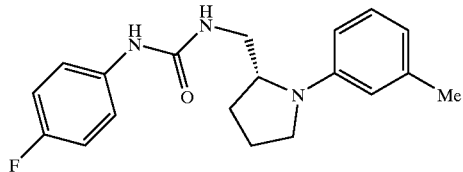

To a solution of ((R)-1-(3-methylphenyl)pyrrolidin-2-yl) methylamine (D7, 0.1 g, 0.5 mmol) in DCM was added 4-fluorophenyl isocyanate (0.072 g, 0.5 mmol). Reaction was stirred at ambient temperature for 1 h and then concentrated under reduced pressure. Chromatography of the residual oil on silica gel eluting with methanol and DCM (gradient elution, 3% maximum) afforded the title compound as a white solid (0.12 g, 73%).

$^1$H NMR (400 MHz, CDCl$_3$) δ 7.15–7.10 (m, 3H), 6.96 (m, 2H), 6.56 (m, 3H), 6.40 (br, 1H), 4.77 (br, 1H), 3.95 (br, 1H), 3.47 (m, 1H), 3.37 (m, 2H), 3.15 (m, 1H), 2.30 (s, 3H), 2.00–1.87 (m, 4H). MH$^+$328

EXAMPLE 2

N-(2-Bromophenyl)-N'-[((R)-1-(3-methylphenyl) pyrrolidin-3-yl)]urea (E2)

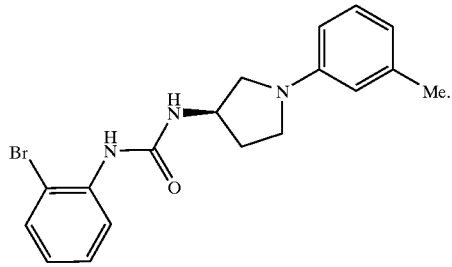

The title compound was prepared from D18 and 2-bromophenyl isocyanate using the procedure outlined for Example 1 (0.12 g, 58%).

¹H NMR (250 MHz, CDCl₃) δ 8.07 (d, 1H), 7.50 (d, 1H), 7.27 (m, 1H), 7.14 (m, 1H), 6.99 (m, 1H), 6.72 (br, 1H), 6.57 (m, 1H), 6.40 (m, 2H), 4.99 (d, 1H), 4.56 (br, 1H), 3.55 (m, 1H) 3.45 (m, 1H), 3.37–3.23 (m. 21, 2.31 (m, 4H) 2.04 (m, 1H). MH⁺374, 376.

The following Examples were prepared using a similar procedures to those disclosed herein and in particular those disclosed for E1 using the appropriate amine and isocyanate.

| Example | Amine | MH⁺ |
|---|---|---|
| N-(2-Bromophenyl)-N'-[((R)-1-(-3-methylphenyl)pyrrolidin-2-ylmethyl)]urea (E3) | D7 | 388, 390 |
| N-(4-Fluorophenyl)-N'-[((S)-1-(3-methylphenyl)pyrrolidin-2-ylmethyl)]urea (E4) | D14 | 328 |
| N-(2-Bromophenyl)-N'-[((S)-1-(3-methylphenyl)pyrrolidin-2-ylmethyl)]urea (E5) | D14 | 388, 390 |
| N-(4-Fluorophenyl)-N'-[((S)-1-(3-methylphenyl)pyrrolidin-3-yl)]urea (E6) | D16 | 314 |
| N-(2-Bromophenyl)-N'-[((S)-1-(3-methylphenyl)pyrrolidin-3-yl)]urea (E7) | D16 | 374, 376 |
| N-(4-Fluorophenyl)-N'-[((R)-1-(3-methylphenyl)pyrrolidin-3-yl)]urea (E8) | D18 | 314 |
| N-(4-Fluorophenyl)-N'-[((R)-1-(3-fluorophenyl)pyrrolidin-3-yl)]urea (E9) | D20 | 317 |
| N-(2-Bromophenyl)-N'-[((R)-1-(3-fluorophenyl)pyrrolidin-3-yl)]urea (E10) | D20 | 378, 380 |
| N-(1-Naphthyl)-N'-[((R)-1-(3-methylphenyl)pyrrolidin-3-yl)]urea (E11) | D18 | 346 |
| N-(2,3-Dichlorophenyl)-N'-[((R)-1-(3-methylphenyl)pyrrolidin-3-yl)]urea (E12) | D18 | 364, 367 |
| N-(2-Bromophenyl)-N'-[((S)-1-(3-fluorophenyl)pyrrolidin-3-yl)]urea (E13) | D28 | 378, 380 |
| N-(2-Bromophenyl)-N'-[((R)-1-(4-fluoro-3-methylphenyl)pyrrolidin-3-yl)]urea (E14) | D26 | 392, 394 |
| N-(2-Bromophenyl)-N'-[((R)-1-(3,4-difluorophenyl)pyrrolidin-3-yl)]urea (E15) | D24 | 396, 398 |
| N-(2-Bromophenyl)-N'-[((R)-1-(3-fluoro-4-methylphenyl)pyrrolidin-3-yl)]urea (E16) | D22 | 392, 394 |
| N-(3-Chloro-2-methylphenyl)-N'-[((R)-1-(3-methylphenyl)pyrrolidin-3-yl)]urea (E17) | D18 | 343, 345 |
| N-(2,3-Dichlorophenyl)-N'-[((R)-1-(3-methylphenyl)pyrrolidin-3-yl)]urea (E18) | D18 | 366, 368 |
| N-(2,5-Dichlorophenyl)-N'-[((R)-1-(3-methylphenyl)pyrrolidin-3-yl)]urea (E19) | D18 | 366, 368 |
| N-(2,3-Dichlorophenyl)-N'-[((R)-1-(3-fluorophenyl)pyrrolidin-3-yl)]urea (E20) | D20 | 369, 371 |
| N-(2,5-Dichlorophenyl)-N'-[((R)-1-(3-fluorophenyl)pyrrolidin-3-yl)]urea (E21) | D20 | 369, 371 |
| N-(3-Chloro-2-methylphenyl)-N'-[((R)-1-(3-fluorophenyl)pyrrolidin-3-yl)]urea (E22) | D20 | 348, 350 |
| N-(3-Chloro-2-methylphenyl)-N'-[((R)-1-(3,4-difluorophenyl)pyrrolidin-3-yl)]urea (E23) | D24 | 367, 369 |
| N-(2,3-Dichlorophenyl)-N'-[((R)-1-(3,4-difluorophenyl)pyrrolidin-3-yl)]urea (E24) | D24 | 388, 390 |
| N-(2,5-Dichlorophenyl)-N'-[((R)-1-(3,4-difluorophenyl)pyrrolidin-3-yl)]urea (E25) | D24 | 388, 390 |
| N-(3-Chloro-2-methylphenyl)-N'-[((R)-1-(3-fluoro-4-methylphenyl)pyrrolidin-3-yl)]urea (E26) | D22 | 362, 364 |
| N-(2,3-Dichlorophenyl)-N'-[((R)-1-(3-fluoro-4-methylphenyl)pyrrolidin-3-yl)]urea (E27) | D22 | 383, 385 |

Pharmacological Data

As referenced above, the compounds of this invention are vanilloid receptor (VR1) antagonists and hence have useful pharmaceutical properties. Vanilloid receptor (VR1) antagonist activity can be determined and demonstrated for any particular compound by use of conventional methods, for example those disclosed in standard reference texts such as D. Le Bars, M. Gozarin and S. W. Cadden, Pharmacological Reviews, 2001, 53(4), 597–652] or such other texts mentioned herein. The screen used for the compounds of this invention was derived from a FLIPR based calcium assay, similar to that described by Smart et al. (British Journal of Pharmacology, 2000, 129, 227–230).

Transfected astrocytoma 1321N1 cells, stably expressing human VR1, were seeded into FLIPR plates at 25,000 cells/well (96-well plate) and cultured overnight. The cells were subsequently loaded in medium containing 4 μM Fluo-3 AM (Molecular Probes) for 2 hours, at room temperature, in the dark. The plates were then washed 4 times with Tyrode containing 1.5 mM calcium, without probenecid.

The cells were pre-incubated with compound or buffer control at room temperature for 30 minutes. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All compounds tested by the above methodology have pKb>6.0 The preferred compounds have pKb>7.0.

What is claimed is:

1. A vanilloid receptor antagonist selected from the group consisting of:

N-(4-Fluorophenyl)-N'-[(R)-1-((3-methylphenyl)pyrrolidin-2-ylmethyl)]urea;

N-(2-Bromophenyl)-N'-[((R)-1-(3-methylphenyl)pyrrolidin-3-yl)]urea;

N-(2-Bromophenyl)-N'-[((R)-1-(3-methylphenyl)pyrrolidin-2-ylmethyl)]urea;

N-(4-Fluorophenyl)-N'-[((S)-1-(3-methylphenyl)pyrrolidin-2-ylmethyl)]urea;

N-(2-Bromophenyl)-N'-[((S)-1-(3-methylphenyl)pyrrolidin-2-ylmethyl)]urea;

N-(4-Fluorophenyl)-N'-[((S)-1-(3-methylphenyl)pyrrolidin-3-yl)]urea;

N-(2-Bromophenyl)-N'-[((S)-1-(3-methylphenyl)pyrrolidin-3-yl)]urea;

N-(4-Fluorophenyl)-N'-[((R)-1-(3-methylphenyl)pyrrolidin-3-yl)]urea;

N-(4-Fluorophenyl)-N'-[((R)-1-(3-fluorophenyl)]pyrrolidin-3-yl)]urea;

N-(2-Bromophenyl)-N'-[((R)-1-(3-fluorophenyl)pyrrolidin-3-yl)]urea;

N-(1-Naphthyl)-N'-[((R)-1-(3-methylphenyl)pyrrolidin-3-yl)]urea;

N-(2,3-Dichlorophenyl)-N'-[((R)-1-(3 -methylphenyl)pyrrolidin-3-yl)]urea;

N-(2-Bromophenyl)-N'-[((S)-1-(3-fluorophenyl)pyrrolidin-3-yl)]urea;

N-(2-Bromophenyl)-N'-[((R)-1-(4-fluoro-3-methylphenyl)pyrrolidin-3-yl)]urea;

N-(2-Bromophenyl)-N'-[((R)-1-(3,4-difluorophenyl)pyrrolidin-3-yl)]urea;

N-(2-Bromophenyl)-N'-[((R)-1-(3-fluoro-4-methylphenyl)pyrrolidin-3-yl)]urea;

N-(3-Chloro-2-methylphenyl)-N'-[((R)-1-(3-methylphenyl)pyrrolidin-3-yl)]urea;

N-(2,3-Dichlorophenyl)-N'-[((R)-1-(3-methylphenyl)pyrrolidin-3-yl)]urea;

N-(2,5-Dichlorophenyl)-N'-[((R)-1-(3-methylphenyl)pyrrolidin-3-yl )]urea;

N-(2,3-Dichlorophenyl)-N'-[((R)-1-(3-fluorophenyl)pyrrolidin-3-yl)]urea;

N-(2,5-Dichlorophenyl)-N'-[((R)-1-(3-fluorophenyl)pyrrolidin-3-yl)]urea;

N-(3-Chloro-2-methylphenyl)-N'-[((R)-1-(3-fluorophenyl)pyrrolidin-3-yl)]urea;

N-(3-Chloro-2-methylphenyl)-N'-[((R)-1-(3,4-difluorophenyl)pyrrolidin-3-yl)]urea;

N-(2,3-Dichlorophenyl)-N'-[((R)-1-(3,4-difluorophenyl)pyrrolidin-3-yl)]urea;

N-(2,5-Dichlorophenyl)-N'-[((R)-1-(3,4-difluorophenyl)pyrrolidin-3-yl)]urea;

N-(3-Chloro-2-methylphenyl)-N'-[((R)-1-(3-fluoro-4-methylphenyl)pyrrolidin-3-yl)]urea; and N-(2,3-Dichlorophenyl)-N'-[((R)-1-(3-fluoro-4-methylphenyl)pyrrolidin-3-yl)]urea; or a pharmaceutically acceptable salt or solvate thereof.

2. A method of treating pain comprising administering a compound according to claim 1 and a pharmaceutically acceptable carrier or excipient.

3. A method for the treatment of diseases or disorders mediated or associated with activity of the vanilloid receptor, wherein said disease or disorder is selected from the group consisting of pain, chronic pain, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, emesis, stomach duodenal ulcer and pruritus; which comprises administering a non toxic, therapeutically effective amount to a patient in need thereof of a compound according to claim 1 or a pharmaceutically acceptable salt or solvate thereof.

* * * * *